United States Patent
Washio et al.

(10) Patent No.: US 10,603,410 B2
(45) Date of Patent: Mar. 31, 2020

(54) COMPLEX OF IMPLANT AND CULTURED PERIODONTAL LIGAMENT CELL SHEET, METHOD FOR MANUFACTURING THE SAME, AND METHOD FOR USING THE SAME

(71) Applicants: Kaoru Washio, Tokyo (JP); Isao Ishikawa, Tokyo (JP); Teruo Okano, Tokyo (JP); GNERAL INC., Niigata (JP)

(72) Inventors: Kaoru Washio, Tokyo (JP); Isao Ishikawa, Tokyo (JP); Teruo Okano, Tokyo (JP); Takao Hanawa, Tokyo (JP); Yusuke Tsutsumi, Tokyo (JP); Yuka Tsumanuma, Tokyo (JP); Supreda Suphanantachat, Bangkok (TH); Kosei Yano, Tokyo (JP)

(73) Assignees: GENERAL INC., Niigata (JP); Kaoru Washio (JP); Isao Ishikawa, Tokyo (JP); Teruo Okano, Tokyo (JP)

( * ) Notice: Subject to any disclaimer, the term of this patent is extended or adjusted under 35 U.S.C. 154(b) by 148 days.

(21) Appl. No.: 15/321,357

(22) PCT Filed: Jun. 24, 2015

(86) PCT No.: PCT/JP2015/068928
§ 371 (c)(1),
(2) Date: Dec. 22, 2016

(87) PCT Pub. No.: WO2015/199245
PCT Pub. Date: Dec. 30, 2015

(65) Prior Publication Data
US 2017/0157292 A1    Jun. 8, 2017

(30) Foreign Application Priority Data

Jun. 24, 2014  (JP) ................................ 2014-129489

(51) Int. Cl.
| | | |
|---|---|---|
| *A61L 27/38* | (2006.01) | |
| *A61L 27/32* | (2006.01) | |
| *A61C 8/00* | (2006.01) | |
| *A61L 27/06* | (2006.01) | |
| *A61L 27/16* | (2006.01) | |
| *A61L 27/36* | (2006.01) | |
| *A61C 8/02* | (2006.01) | |

(52) U.S. Cl.
CPC .......... *A61L 27/3865* (2013.01); *A61L 27/06* (2013.01); *A61L 27/16* (2013.01); *A61L 27/32* (2013.01); *A61L 27/3687* (2013.01); *A61L 27/3691* (2013.01); *A61L 27/3804* (2013.01); *A61L 27/3895* (2013.01); *A61C 8/005* (2013.01); *A61C 8/0006* (2013.01); *A61C 8/0012* (2013.01); *A61L 2430/12* (2013.01)

(58) Field of Classification Search
CPC ...... A61L 27/3865; A61L 27/06; A61L 27/32; A61L 27/3804; A61L 2430/12; A61C 8/0006; A61C 8/0012
See application file for complete search history.

(56) References Cited

U.S. PATENT DOCUMENTS

| 9,114,192 B2 | 8/2015 | Okano et al. |
|---|---|---|
| 2004/0009566 A1 | 1/2004 | Okano et al. |
| 2005/0069570 A1 | 3/2005 | Ishibashi et al. |
| 2008/0118474 A1 | 5/2008 | Okano et al. |
| 2011/0212418 A1 | 9/2011 | Nakahara et al. |

FOREIGN PATENT DOCUMENTS

| EP | 2 527 427 | 11/2012 |
|---|---|---|
| JP | 2002119522 | 4/2002 |
| JP | 2006-130007 | 5/2006 |
| JP | 2006-255319 | 9/2006 |
| JP | 4475847 | 6/2010 |
| JP | 2013-85927 | 5/2013 |
| WO | 2006/068972 | 6/2006 |

OTHER PUBLICATIONS

Dan et al., The influence of cellular source on periodontal regeneration using calcium phosphate coated polycaprolactone scaffold supported cell sheets. Biomaterials, vol. 35, No. 1 (online Oct. 10, 2013) pp. 113-122. (Year: 2013).*
Guéhennec et al., Surface treatments of titanium dental implants for rapid osseointegration. Dental Materials, vol. 23, No. 7 (Jul. 2007) pp. 844-854. (Year: 2007).*
International Search Report dated Oct. 6, 2015 in International (PCT) Application No. PCT/JP2015/068928.
Choi, "Periodontal Ligament Formation Around Titanium Implants Using Cultured Periodontal Ligament Cells: A Pilot Study", The International Journal of Oral & Maxillofacial Implants, vol. 15, 2000, pp. 193-196.
Palaiologou et al., "Altered Cell Motility and Attachment With Titanium Surface Modifications", J. Periodontal, vol. 83, 2012, pp. 90-100.
Kano et al., "Regeneration of Periodontal Ligament for Apatite-coated Tooth-shaped Titanium Implants with and without Occlusion Using Rat Molar Model", Journal of Hard Tissue Biology, vol. 21, No. 2, 2012, pp. 189-202.
Wei et al., "Functional Tooth Restoration by Allogeneic Mesenchymal Stem Cell-Based Bio-Root Regeneration in Swine", Stem Cells and Development, vol. 22, No. 12, Nov. 12, 2013, pp. 1752-1762.
Tsutsumi et al., "Attempts to Regenerate Periodontal Tissues Like Periodontol Ligaments Around Implantations", The Journal of the Tokyo Dental Association, vol. 57, No. 10, 2009, pp. 499-504, with partial translation.

(Continued)

*Primary Examiner* — Kara D Johnson
(74) *Attorney, Agent, or Firm* — Wenderoth, Lind & Ponack, L.L.P.

(57) ABSTRACT

A complex of implant and cultured periodontal ligament cell sheet, that can be satisfactorily stabilized into the bone through periodontal ligament tissue, is provided. A fixture of the inserted implant is coated with calcium phosphate and the cultured periodontal ligament cell sheet is brought into intimate contact with the implant.

9 Claims, 9 Drawing Sheets

(56) References Cited

OTHER PUBLICATIONS

"Issues with Dental Implant Treatment Focusing on Physical Health Problems", National Consumer Affairs Center of Japan, http://www.kokusen.go.jp/pdf/n-20111222_2.pdf, 2011, pp. 1-23, with partial translation.
Mombelli et al., "The diagnosis and treatment of peri-implantitis", Periodontology 2000, vol. 17, 1998, pp. 63-76.
Gault et al., "Tissue-engineered ligament: implant constructs for tooth replacement", J. Clin. Periodontol, vol. 37, 2010, pp. 750-758.
Wei et al., "Functional Tooth Restoration by Allogeneic Mesenchymal Stem Cell-Based Bio-Root Regeneration in Swine", Stem Cells and Development, vol. 22, No. 12, 2013, pp. 1752-1762.
Tsutsumi et al., "Attempts to Regenerate Periodontal Tissues Like Periodontal Ligaments Around Implantations", The Journal of the Tokyo Dental Association, vol. 57, No. 10, 2009, pp. 499-504, with partial translation.
Extended European Search Report dated Sep. 15, 2017 in European Application No. 15811015.5.
Flores et al., "Periodontal ligament cell sheet promotes periodontal regeneration in athymic rats", Journal of Clinical Periodontology, 35(12):1066-1072 (2008).
Hasegawa et al., "Human Periodontal Ligament Cell Sheets Can Regenerate Periodontal Ligament Tissue in an Athymic Rat Model", Tissue Engineering, 11(3/4):469-478 (2005).
Notice of Reasons for Refusal dated Jun. 4, 2019 in Japanese Patent Application No. 2016-529689, with Machine Translation.
Tsuda et al., "Intelligent Surfaces for Medical Applications", Journal of the Surface Science Society of Japan, 2006, vol. 27, No. 3, pp. 176-181, with Partial Translation.

\* cited by examiner

After blasting and acid treatment
($R_a = 0.703$ μm)

After immersion in Hanks solution
($R_a = 0.364$ μm)

Length of adhesion: about 140 μm

Calcium phosphate : (−)

Length of adhesion: about 600 μm

Calcium phosphate : (+)

COMPLEX OF IMPLANT AND CULTURED PERIODONTAL LIGAMENT CELL SHEET, METHOD FOR MANUFACTURING THE SAME, AND METHOD FOR USING THE SAME

TECHNICAL FIELD

This invention relates to a complex of implant and cultured periodontal ligament cell sheet, methods for manufacturing the same, as well as therapeutic methods using the same, in fields of biology, medicine, and the like.

BACKGROUND ART

Japan has become an aging society, with the average life span in Japan being the longest in the world. People now focus on the quality of life (QOL), that is, living a better life, rather than simply living longer. Speaking and eating are important functions especially for elderly people, which lead to a reason for living. In that sense, health maintenance for masticatory organs, including maintenance of teeth, can be said to be a factor that significantly influences QOL. Mastication is a function indispensable for ingestion of food. Moreover, it is becoming clear, from recent studies on the mastication system, that mastication influences various systemic functions in the entire body, for example, mastication stimulates brain cells to promote mental/neural development and activation, enhances the immune function, and furthermore, suppresses obesity. Thus, a decrease in the masticatory function due to loss of teeth may lead to occurrence of dementia, lifestyle-related diseases, and the like.

Teeth are exposed to the oral cavity breaking through the epithelium, and continuity of the epithelium disappear at the boundaries between teeth and gingiva. Thus, teeth are in a very special environment in the body. Teeth and gingiva are constituted by "epithelial attachment" and "connective tissue attachment". In the former attachment, an epithelium called junctional epithelium adheres to the tooth surface (enamel) through hemidesmosomes and the basal lamina. The latter attachment is constituted by the periodontal ligament. Collagen fibers are inserted into root surface cementum while their calcification proceeds, and those fibers are inserted into alveolar bone similarly while their calcification proceeds, providing gingival fibers. By this, teeth are strongly bound to alveolar bone and gingiva.

The periodontal ligament is an aggregate of periodontal ligament fibers, and, as described above, those fibers run almost perpendicularly to the tooth surface and the alveolar bone surface in most cases. The run of those fibers plays a role as a cushion that reduces the force applied to the teeth. It reduces mechanical loads on the teeth such as the force due to improper occlusion, or bruxism. The periodontal ligament also plays a role in transmitting a delicate sense felt upon chewing to the brain. By this, hardness of the object chewed can be recognized, and hence an object can be chewed with an appropriate force, so that unnecessary injury of teeth and gingiva can be avoided. The periodontal ligament is rich in blood vessels, and has abundant supply of blood. Therefore, during inflammation, the periodontal ligament can protect against infection by recruiting leukocytes.

Methods using a denture or a bridge have been mainly used for replacing a tooth that was lost by dental caries, periodontal disease, or the like. However, in recent years, therapeutic methods using a dental implant, which is aesthetic and functional, and does not require cutting preparation of adjacent teeth, are attracting attention. The implant treatment means a treatment in which a titanium or titanium alloy support is embedded in the jawbone in a place where a tooth is lost, and the artificial tooth is repaired using the support as a base. According to a recent survey, implant treatment has become a common dental treatment in Japan (Non-patent Document 1), received by 1 or 2 out of 50 adults who are 30 years of age or older. An implant is composed of a fixture (artificial tooth root), an abutment (connecting portion), and an upper structure (artificial tooth crown). In the basic flow of implant treatment, the fixture section of the implant is embedded in the bone, and, after sufficient adhesion of the fixture to the bone, a crown is formed on the upper structure. The process of adhesion of the fixture to the bone is called osseointegration, and it usually requires a period of 2 to 6 months. In cases where an operation for increasing bone or the like is necessary before embedding the fixture, a period of not less than one year is sometimes required. The ten-year implant survival rate is almost 90% or more, which is influenced by the age of the patient and implant system selection, and the like. The patients who visit implant treatment facilities are young on an average, but some data also show that patients who receive the treatment most frequently are in the age groups of forties and fifties that have significant influence of periodontal disease and the like.

However, various problems have also been pointed out for the implant method. For successful implant treatment, it is important to achieve sufficient adhesion of the implant to the bone, and to allow stabilization of the implant in the jawbone so that movement of the implant does not occur therein. There are a significant number of cases where implantation failed due to failure in achieving such stabilization. In a physiologically normal state, a connective tissue called periodontal ligament tissue is present in the vicinity of a tooth. Since, as described above, the periodontal ligament tissue fills the space between the tooth and the alveolar bone to function as a cushion material, the mechanical load on the tooth can be reduced, and inflammation that occurred in the vicinity of the tooth can be ameliorated, so that influences on the surrounding bone can be suppressed.

In current implant treatment, a biocompatible metal such as titanium is screwed into the jawbone, so that the implant is fixed in a state where the metal is in contact with, and adhering to, the bone. In this method, there is no periodontal ligament tissue surrounding the implant, and angiogenesis is unlikely to occur. Therefore, once inflammation occurs, migration of immune cells to suppress the inflammation is difficult, and the inflammation is likely to show direct and extensive spread to the bone (peri-implantitis) (Non-patent Document 2). Moreover, an implant is likely to cause detachment of gingiva because of the absence of the connective tissue attachment, and inflammation easily progresses once it occurs, leading to difficulty in curing of the inflammation. There is no appropriate therapeutic method for such symptoms, which is problematic.

When the development of the implant initially started, the fixture section had a smooth surface, and it was called the cylinder type. Thereafter, it was found that a screw-shaped fixture section is advantageous in the initial fixation, so that the current implant is of a type having a screw thread. More recently, an implant having a fixture section coated with HA (hydroxyapatite) was developed in order to allow faster and stronger binding to bone. Since HA has components similar to components in the living body, it can be expected to show bone-conducting capacity in osteogenesis. There is actually a result of an experiment which shows that, while an HA-coated implant shows formation of bone to a distance of 1.5 mm around the implant, an HA-uncoated implant (with a titanium surface) allows formation of bone to a distance of up to only 0.3 mm around the implant. In Japan, a variety of production methods have been developed in 1990s. In particular, implants coated with recrystallized HA have been widely applied to clinical use as implants with which early bone induction can be expected. More recently, it was found that a stronger bond to the bone can achieved by surface treatment with a strong acid rather than by blasting. After this discovery, surface properties of implants have been improved by preparation of rough surfaces (micro-rough structures) on implants by blasting or strong acid treatment. Currently, attempts are being made to cause osteoconduction and calcification by fluorine coating of the implant surface to thereby accelerate the cure, but no implant has completely solved the problems so far.

On the other hand, studies on treatment of periodontal disease, which is considered to be a cause of tooth loss, by transplantation of cells are being actively carried out in recent years. In many of these studies, single cells are plated on a three-dimensional matrix, and the matrix is then implanted by injection into a site where a tissue is lost. For example, Non-patent Document 3 describes that, by culturing cells separated from periodontal ligament in the vicinity of a titanium implant to allow formation of a plurality of cell layers on the implant surface, and then inserting the implant in an affected site, alveolar bone and the like could be formed in the vicinity of the implant. However, construction of an expected tissue has not been realized yet. Possible reasons for this failure are difficulties in selection of the cell source, and in control of localization of cell differentiation in the site where a tissue is lost. For regeneration of a periodontal tissue, cementum needs to be newly generated on the root surface. Therefore, not only the periodontal ligament, which is a soft tissue, but also the cementum or the alveolar bone, which is a hard tissue, need to be regenerated at the same time to allow their functional connection to each other. If these tissues are formed at different times depending on actions of progenitor cells and growth factors specific to the tissues, the cell transplantation method in the regeneration of the periodontal tissue needs to be more delicate. That is, the transplantation requires definition of places where cells are to be arranged, and arrangement of appropriate cells in each of those places, rather than simply injecting single cells to the lost portion after space making, and allowing tissue differentiation in the living body.

Preparation of the cells required in this process has been carried out by culture on a glass surface, or on a surface of a synthetic polymer subjected to various treatments. For example, various containers and the like made of polystyrene subjected to surface treatment such as γ-ray irradiation or silicone coating are commonly used as cell culture vessels. Cells cultured/grown using such cell culture vessels are detached and collected from the surface of the vessels by treatment with a protease such as trypsin, or a chemical agent. However, collection of grown cells by the chemical treatment described above has been pointed out to have drawbacks such as a laborious treatment process, high possibility of contamination, and possible degeneration or damaging of the grown cells by the chemical treatment, which may lead to deterioration of intrinsic functions of the cells.

In order to overcome such drawbacks, several techniques have been proposed so far. In particular, Patent Document 1 enabled preparation of a cell sheet having sufficient strength by culturing anterior ocular segment-related cells on a cell culture support formed by coating the surface of a base material with a temperature responsive polymer of which upper or lower critical solution temperature against water is 0 to 80° C., layering, if necessary, a cultured cell layer thereon by a conventional method, and then detaching the cultured cell sheet simply by changing the temperature of the support. The cell sheet also retains basal lamina-like protein, and shows obviously better engraftment on a tissue compared to the dispase-treated cells described above. In Patent Document 2, it was discovered that a cardiac muscle-like cell sheet can be constructed by culturing cardiac muscle tissue cells on a cell culture support of which surface is grafted with a temperature responsive polymer. It was also discovered that the cell sheets have less structural defects and several functions as a cardiac muscle-like tissue in vitro by changing the temperature of the culture medium not to less than the upper critical solution temperature or not more than the lower critical solution temperature, bringing the layered cell sheet into close contact with a polymer membrane, detaching the cell sheet together with the polymer membrane, and then forming the resultant three-dimensional structure by a predetermined method.

Patent Document 3 shows that, when periodontal ligament tissue cells are cultured on a cell culture support of which surface is grafted with a temperature responsive polymer to obtain a periodontal ligament cell sheet, the cultured periodontal ligament cell sheet can be detached by changing the temperature of the culture medium not to less than the upper critical solution temperature or not more than the lower critical solution temperature. And it also shows that regeneration of a periodontal tissue containing a periodontal ligament tissue can be induced by attaching the periodontal ligament cell sheet to the root of a natural tooth. Patent Document 4 describes a method for regenerating a periodontal tissue by wrapping the crown or the root of a natural tooth with a periodontal ligament cell sheet. However, none of these methods have been carried out aiming to solve the problems on engraftment and fixation of implants made of a metal such as titanium.

PRIOR ART DOCUMENTS

Patent Documents

Patent Document 1: JP 4475847 B
Patent Document 2: JP 4679795 B
Patent Document 3: JP 4827729 B
Patent Document 4: WO 2010/027008

Non-Patent Documents

Non-patent Document 1: Survey by National Consumer Affairs Center of Japan, 2011 [online], [search on May 30, 2014], Internet <URL:http://www.kokusen.go.jp/pdf/n-20111222_2.pdf>
Non-patent Document 2: Periodontology 2000, 17.1, 63-76 (1998) Non-patent Document 3: Journal of Clinical Periodontology, 37.8, 750-758 (2010)

SUMMARY OF THE INVENTION

Problems to be Solved by the Invention

This invention relates to techniques for wrapping an implant body with a cultured periodontal ligament cell sheet. On the other hand, the patent and non-patent documents described above are significantly different from this invention because the documents showed the method transplanting cell sheets to a natural tooth, but this invention targets to an implant made of a metal such as titanium, which is an artificial product. This invention was made for the purpose of solving the problems of conventional techniques described above. That is, an object of this invention is to provide a complex of implant and cultured periodontal ligament cell sheet which enables favorable adhesion and stabilization of an implanted implant to bone through the periodontal ligament. Another object of this invention is to provide a method for producing it, and a method for using it.

Means for Solving the Problems

In order to solve the problems described above, the inventors carried out research and development by performing studies from various viewpoints. As a result, it was discovered that, by coating the surface of a dental implant fixture section with calcium phosphate, and bringing a cultured periodontal ligament cell sheet into close contact with the fixture section, a calcified structure can be formed on the surface of the implanted implant, and that the implant can be extremely favorably stabilized to bone via a periodontal ligament-like tissue formed directly on the calcified structure. This invention was made based on such findings.

That is, this invention provides a complex of implant and cultured periodontal ligament cell sheet which can be favorably stabilized to bone through a cementum-like hard tissue and a periodontal ligament-like tissue formed in the vicinity of the implant.

This invention also provides a therapeutic method in which a lost tooth is replaced by implantation of the complex of the implant and cultured periodontal ligament cell sheet.

Effect of the Invention

By using the complex of the implant and cultured periodontal ligament cell sheet of this invention, a periodontal tissue-like tissue can be formed in the adjacent of the implant, so that the implant can be stabilized to alveolar bone in an environment similar to the physiologically normal state. This invention is expected to be applied especially to the dental field. It is considered that, by preparing a cell bank for cryopreservation of cells, this invention can be applied to a larger number of patients.

EMBODIMENTS FOR CARRYING OUT THE INVENTION

Figure 1:
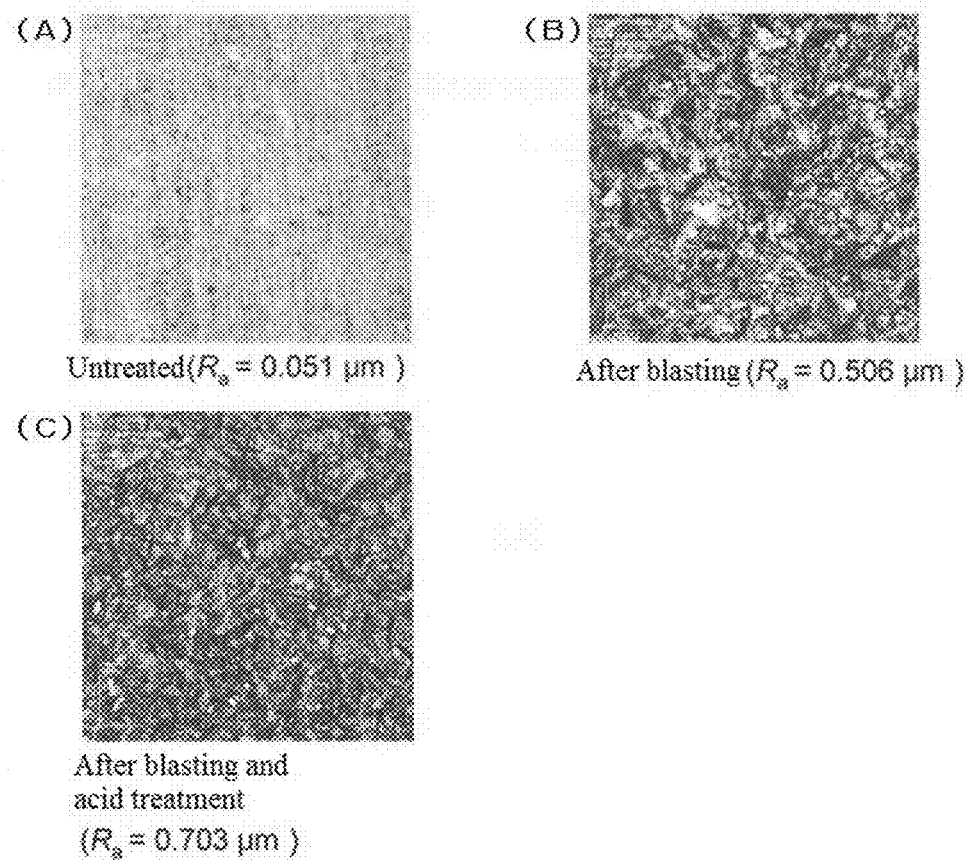
FIG. 1 shows scanning electron micrographs showing changes on the surfaces of surface-treated titanium foils. Panel (A): untreated; Panel (B): after blasting; Panel (C): after blasting and acid treatment.

This invention relates to adhesion of a cultured human periodontal ligament cell sheet to the periphery of the fixture section of an implant, and includes the followings.

[1] A complex of implant and cultured periodontal ligament cell sheet, wherein the implant contains a fixture section; the surface of the fixture section is coated with calcium phosphate; and a cultured periodontal ligament cell sheet is in close contact with the surface thereof.

[2] The complex of the implant and cultured periodontal ligament cell sheet according to [1], wherein the cultured periodontal ligament cell sheet is obtained by culturing periodontal ligament cells on a cell culture support formed by coating a surface of a base material with a temperature responsive polymer whose upper or lower critical solution temperature against water is 0 to 80° C., and detaching the cultured cells by changing the temperature of a culture medium to not less than the upper critical solution temperature or to not more than the lower critical solution temperature.

[3] The complex of the implant and cultured periodontal ligament cell sheet according to [2], wherein the temperature responsive polymer is poly(N-isopropylacrylamide).

[4] The complex of the implant and cultured periodontal ligament cell sheet according to any one of [1] to [3], wherein the cultured periodontal ligament cell sheet is a calcification-induced cultured periodontal ligament cell sheet.

[5] The complex of the implant and cultured periodontal ligament cell sheet according to [4], wherein the calcification-induced cultured periodontal ligament cell sheet is a cultured periodontal ligament cell sheet cultured in a medium containing dexamethasone, ascorbic acid, and β-glycerophosphate.

[6] The complex of the implant and cultured periodontal ligament cell sheet according to any one of [1] to [5], wherein the cultured periodontal ligament cell sheet is a layered sheet.

[7] The complex of the implant and cultured periodontal ligament cell sheet according to any one of [1] to [6], wherein the fixture section has a surface roughened by blasting and acid treatment, the surface having an arithmetic average roughness (Ra) of 0.1 to 1.0 μm.

[8] The complex of the implant and cultured periodontal ligament cell sheet according to any one of [1] to [7], wherein the material of the fixture section is titanium.

[9] The complex of the implant and cultured periodontal ligament cell sheet according to any one of [1] to [8], wherein the fixture section has a cylindrical shape.

[10] The complex of the implant and cultured periodontal ligament cell sheet according to any one of [1] to [9], for use in treatment for replacing the lost tooth.

[11] The complex of the implant and cultured periodontal ligament cell sheet according to [10], wherein the treatment comprises bringing a cultured periodontal ligament cell sheet into close contact with a dental implant fixture section, followed by implantation and stabilization to jaw bone.

[12] The complex of the implant and cultured periodontal ligament cell sheet according to [10] or [11], wherein the treatment is replacing a lost tooth.

[13] A dental implant fixture cultured periodontal ligament cell sheet complex, wherein the surface of the fixture is coated with calcium phosphate, and the cultured periodontal ligament cell sheet is in close contact with the surface thereof.

Similarly to the cases of natural teeth described in the above documents, direct application of the cultured periodontal ligament cell sheet to titanium itself resulted in failure to obtain an image in which, as can be seen in the vicinity of a natural tooth, a periodontal ligament-like tissue (fibrous connective tissue) runs such that a tooth and bone are connected to each other. Thus, only bone adhesion as can be seen in conventional implant methods was found. In view of this, the inventors discovered that cell adhesion can be improved by carrying out surface treatment such as calcium phosphate coating also on the titanium side, and that a calcified layer can be formed on the titanium more extensively by using a calcification-inducing medium for the cultured periodontal ligament cell sheet. The inventors further discovered that this allows formation of a periodontal ligament-like tissue derived from implanted cells between the calcified layer and alveolar bone, and hence enables mimicking of a tissue structure found in the vicinity of a natural tooth such that periodontal ligament fibers run perpendicularly to the implant root. Such a phenomenon cannot be assumed at all based on conventional techniques, and was elucidated for the first time by this invention. There have been reports on various methods for fixation of a titanium implant to jaw bone in the world. However, a physiologically normal run of periodontal ligament fibers could not be found in any of their results. The impact of practical application of this invention may be so strong that all conventional implant treatment methods may be replaced by this method, and, from the viewpoint of the market size and the like, this method may have an extremely large influence on the economy. Therapeutic methods based on conventional techniques are periodontal treatment techniques which take into account repair and regeneration for a bone defect caused by periodontal disease of a diseased tooth. Since, in this invention, an implant root having the same functions as those of a natural tooth can be regenerated, people can retain the entire dentition of functional teeth throughout the life. Thus, this invention can completely change the conventional concept of dentistry by allowing sufficient mastication, providing aesthetic appearance, and largely contributing to the health of people.

The calcium phosphate in the calcium phosphate coating in this invention is not limited as long as it is a compound having a calcium ion and a phosphate ion as constituents. Specific examples of the calcium phosphate include hydroxyapatite, carbonate apatite, calcium dihydrogen phosphate, calcium hydrogen phosphate, calcium phosphate, calcium octaphosphate, tetracalcium phosphate, and hydrates thereof. These may be used individually, or two or more of these may be used in combination.

The method for the coating with calcium phosphate is not limited as long as it is a coating method for an implant. Examples of the method include immersion in a solution containing phosphate ions and calcium ions for 5 to 30 days, preferably 10 to 20 days, more preferably 14 to 17 days. The temperature during the immersion may be 10 to 50° C., preferably 20 to 45° C., more preferably 30 to 40° C.

Examples of the solution containing phosphate ions and calcium ions include, but are not limited to, simulated body fluids such as Hanks solution and Kokubo solution (simulated body fluid; SBF), and equivalents thereof. Examples of the equivalents include solutions having compositions different from those of simulated body fluids such as Hanks solution and Kokubo solution, as long as the difference does not affect the calcium phosphate formation, or promotes the calcium phosphate formation. Thus, examples of the equivalents of the simulated body fluids include those at higher concentrations, such as those at 1.5 to 2.0 times the concentration of Hanks solution or Kokubo solution, from the viewpoint of promoting the calcium phosphate formation.

The phosphate ion concentration in the solution is not limited. The concentration is, for example, $1.0 \times 10^{-3}$ to $100.0$ mM, preferably $1.0 \times 10^{-2}$ to $10.0$ mM, more preferably $1.0 \times 10^{-1}$ to $1.0$ mM.

The calcium ion concentration in the solution is not limited. The concentration is, for example, $5.0 \times 10^{-3}$ to 500.0 mM, preferably $5.0 \times 10^{-2}$ to 50.0 mM, more preferably 0.5 to 5 mM.

The pH of the solution containing phosphate ions and calcium ions may be set appropriately within the range in which the surface of the implant can be coated with calcium phosphate. The pH is, for example, 6 to 10, preferably 7 to 9.

The coating may be carried out either separately or in combination with one or more other treatments. The coating is preferably carried out after the surface roughening described below.

An implant is composed of a fixture (artificial tooth root), an abutment (connecting portion), and an upper structure (artificial tooth crown). The fixture is the portion to be embedded in the alveolar bone. The abutment is attached to the fixture, and the artificial tooth which is the upper structure is attached to the abutment. The fixture and the abutment are integrated with each other in some cases. Any implant is included within the scope of this invention as long as the implant is coated with calcium phosphate and contains a fixture that is in close contact with a cultured periodontal ligament cell sheet. That is, the implant in this invention may be only a fixture, a fixture and an abutment, or a fixture and an abutment integrated with each other. The upper structure may be either fixed to the abutment, or may be a removable overdenture. The implant in this invention is preferably one in which the surface of the fixture is subjected to surface roughening. By this treatment, efficient adhesion of cells on the surface of the fixture section is possible, so that the treatment is very effective for embedding of the implant to the bone. In terms of an index of the surface roughness in this treatment, the complex of the implant and cultured periodontal ligament cell sheet of this invention preferably has a surface with an arithmetic average roughness (Ra), as defined by JIS B 0601:2001, of about 0.1 to 1.0 μm.

In this invention, the surface roughening method is not limited. Examples of the method include blasting, acid treatment, and phosphate treatment.

Examples of the blasting include, but are not limited to, sand blasting using "sand" such as silica sand or zirconia powder, shot blasting using steel balls, and grit blasting using crushed steel balls or an angular material.

Examples of the acid to be used in the acid treatment include, but are not limited to, hydrogen peroxide, sulfuric acid, hydrochloric acid, and nitric acid.

Examples of the phosphate to be used in the phosphate treatment include, but are not limited to, calcium phosphate and hydroxyapatite.

The rough surface preparation methods described above may be carried out individually, or two or more of these may be carried out in combination.

The implant in this invention is not limited, and may be an implant that is conventionally used. The material of the fixture section is not limited in this invention, and examples of the material include pure titanium, titanium alloy, and zirconia. The shape of the fixture section is also not limited. The fixture section may be of a screw type, which is provided with a screw thread; a cylinder type, which does not have a screw thread; a basket type, which has a hollow shape; or a blade type. For the other portions of the implant, that is, the abutment and the upper structure, those conventionally used may be used without limitation. Examples of the method for fixing the abutment to the fixture include the screw method and the dental cement fixation method, as well as use of a one-piece type in which the abutment and the fixture are integrated with each other. Examples of the material of the abutment include titanium alloy and zirconia. Examples of the method for fixing the upper structure to the abutment include the screw method and the dental cement fixation method. Examples of the material of the upper structure include gold-silver-palladium alloys and ceramics.

The cultured periodontal ligament cell sheet in this invention is preferably prepared by culturing periodontal ligament cells on a cell culture support formed by coating a surface of a base material with a temperature responsive polymer whose upper or lower critical solution temperature against water is 0 to 80° C., and detaching the cultured cells by changing the temperature of a culture medium to not less than the upper critical solution temperature or to not more than the lower critical solution temperature. In cases where the cells are detached without using trypsin or the like, a large amount of adhesive proteins produced by the cells themselves during the culture are present on the lower-side surface of the cell sheet. Thus, the cultured periodontal ligament cell sheet shows excellent adhesion to the surface of the implant.

The cultured periodontal ligament cell sheet to be used in this invention may be a calcification-induced cell sheet. This more easily allows differentiation induction of a part of the implanted cells into a cementum-like tissue that can be used as a scaffold for the periodontal ligament tissue, and formation of the tissue on the implant surface.

The method of induction of calcification is not limited, and examples of the method include, but are not limited to, a method in which culture is carried out in a medium containing one or more of dexamethasone, ascorbic acid, and β-glycerophosphate. The timing of addition of these components into the medium may be the beginning of the culture, or may be Day 2, Day 3, or Day 4 of the culture, or even later. In terms of the length of the period of addition of those components, they may be added for about 1 to 3 weeks from the beginning of the addition, or the addition may be continued even after the cells became confluent.

In this invention, other components in the medium composition are not limited, and may be those normally used for culturing the cells described above. For example, the medium for culturing a cell sheet of periodontal ligament fibroblasts, or of a mixture of periodontal ligament fibroblasts and at least one type of cells selected from cementoblasts, osteoblasts, gingival fibroblasts, and vascular endothelial cells, may be α-MEM medium, DMEM medium, or a medium prepared by adding 10% bovine serum to their mixture.

The type of the cells to be used for the preparation of the complex of the implant and cultured periodontal ligament cell sheet of this invention is not limited, and preferred examples of the cells include: periodontal ligament fibroblasts; and mixtures of the periodontal ligament fibroblasts and at least one type of cells selected from cementoblasts, osteoblasts, gingival fibroblasts, and vascular endothelial cells. In this invention, the cultured periodontal ligament cell sheet means a sheet prepared by culturing the cells on a culture support to allow formation of a single layer, and then detaching the layer from the support. The resulting cell sheet has a lower-side surface, which was in contact with the culture support during the culture, and an upper-side surface, which corresponds to the opposite side thereof.

The cultured periodontal ligament cell sheet in this invention may be a single-layered sheet of the periodontal ligament fibroblasts described above, or of a mixture of the periodontal ligament fibroblasts and at least one type of cells selected from cementoblasts, osteoblasts, gingival fibroblasts, and vascular endothelial cells. The cultured periodontal ligament cell sheet may also be a layered sheet prepared with the single-layer sheet. The layered sheet herein may be a sheet composed of the cultured periodontal ligament cell sheet alone, or may be in a state where the cultured periodontal ligament cell sheet is combined with a sheet(s) composed of other cells. Examples of the layered sheet include, but are not limited to, sheets prepared by layering cell sheets of the periodontal ligament fibroblasts, or of a mixture of the periodontal ligament fibroblasts and at least one type of cells selected from cementoblasts, osteoblasts, gingival fibroblasts, and vascular endothelial cells on each other; and sheets prepared by layering a cultured cell sheet(s) composed of at least one type of other cells selected from cementoblasts, osteoblasts, and gingival fibroblasts on the above-described single-layered cell sheet. The position, the order, and the number of times of the layering are not limited, and examples of the layered sheet include:

a layered sheet in which the same cell sheet(s) is/are layered on at least one or both of the lower side and the upper side of a single-layered cell sheet composed of the periodontal ligament fibroblasts or of a mixture of the periodontal ligament fibroblasts and at least one type of cells selected from cementoblasts, osteoblasts, gingival fibroblasts, and vascular endothelial cells;

a layered sheet in which a cell sheet(s) composed of at least one type of other cells selected from cementoblasts, osteoblasts, and gingival fibroblasts is/are layered on at least one or both of the lower side and the upper side of the above-described single-layered cell sheet; and a layered sheet in which the same cell sheet(s) and a cell sheet(s) composed of at least one type of other cells selected from cementoblasts, osteoblasts, and gingival fibroblasts are layered on the above-described single-layered cell sheet.

The layered sheet may also be a layered sheet in which a cell sheet composed of osteoblasts is layered on the upper side of a single-layered cell sheet composed of periodontal ligament fibroblasts or of a mixture of the periodontal ligament fibroblasts and at least one type of cells selected from cementoblasts, osteoblasts, gingival fibroblasts, and vascular endothelial cells, and a cell sheet composed of cementoblasts is layered on the lower side; or a layered sheet in which a cell sheet composed of gingival fibroblasts is layered on the upper side of a single-layered cell sheet composed of periodontal ligament fibroblasts or of a mixture of the periodontal ligament fibroblasts and at least one type of cells selected from cementoblasts, osteoblasts, gingival fibroblasts, and vascular endothelial cells, and a cell sheet composed of osteoblasts is further layered thereon, followed by layering a cell sheet composed of cementoblasts on the lower side.

The number of times of the layering is preferably not more than 8, more preferably not more than 6, still more preferably not more than 4. In cases where the number of times of the layering is more than 8, oxygen and nutrients do not reach a cell sheet(s) positioned in the middle of the layered sheet. This is not preferred since cell death may occur.

The cultured periodontal ligament cell sheet in this invention is preferably one which is not damaged during the cell detachment by a protease such as dispase or trypsin. Thus, the cultured periodontal ligament cell sheet detached from the base material retains the desmosome structure between the cells, hardly shows a structural deficit, and has high strength. In the cultured periodontal ligament cell sheet in this invention, the basal lamina-like protein formed during the culture between the cells and the base material is also preferably one which is not damaged by enzyme. Because of this, the cultured periodontal ligament cell sheet can favorably adhere to the affected tissue, and enables efficient treatment. That is, more specifically, in cases where a conventional protease such as trypsin is used, the desmosome structures between the cells, the basal lamina-like protein between the cells and the base material, and the like are hardly retained, so that the cells are detached in a state where they are separated from each other. Among proteases, dispase is known to be capable of detaching cells while retaining 10 to 60% of the desmosome structures between the cells. However, since dispase destroys most of the basal lamina-like protein between the cells and the base material, the obtained cell sheet has only weak strength. In contrast, the cell sheet in this invention is in a state where not less than 80% of the desmosome structures and the basal lamina-like protein are maintained, so that the various effects described above can be obtained therewith.

The cultured periodontal ligament cell sheet in this invention shows very favorable engraftment on implants. Such a property can be realized by suppressing excessive contraction of the cultured periodontal ligament cell sheet detached from the surface of the support. In this process, the contraction rate of the cultured periodontal ligament cell sheet is preferably not more than 50%, more preferably not more than 30%, still more preferably not more than 20%, in any of the directions in the sheet. In cases where the contraction rate is not less than 50% in one or more directions in the sheet, the cell sheet often forms a cluster after the detachment. When the cell sheet in this state is attached to a body tissue, close contact of the cell sheet with the tissue can be hardly achieved.

The method for preventing excessive contraction of the cultured periodontal ligament cell sheet is not limited. Examples of the method include a method in which a carrier or the like is brought into close contact with the cultured periodontal ligament cell sheet before detaching the cell sheet from the support, and the cell sheet is then detached together with the carrier.

The carrier to be brought into close contact with the cultured periodontal ligament cell sheet is a structure for retaining the cell sheet in this invention to prevent its excessive contraction. Examples of the carrier include polymer films; structures formed from polymer films; and metal jigs. In cases where a polymer is used as the material of the carrier, specific examples of the material include polyglycolic acid, polyvinylidene difluoride (PVDF), polypropylene, polyethylene, cellulose and derivatives thereof; paper, chitin, chitosan, collagen, and urethane.

The close contact in this invention is a state where slippage or movement of the cell sheet on the carrier is prevented on the interface between the cell sheet and the carrier so that the cell sheet does not undergo excessive contraction. The close contact may be achieved by physical binding or through a liquid (for example, a culture medium or another isotonic solution) present between the cell sheet and the carrier.

The shape of the carrier is not limited. The carrier may be designed appropriately depending on, for example, the type of the cells and the shape of the culture dish or the implant.

The culture period of the cultured periodontal ligament cell sheet in this invention is not limited. The culture period is preferably not more than 21 days, more preferably not more than 15 days, still more preferably not more than 10 days, after the cells became confluent (fully grown). In cases where the culture period is longer than 21 days, the activity of the cells in the bottom layer of the complex of the implant and cultured periodontal ligament cell sheet decreases, leading to decreased adhesion in some cases.

The portion of the fixture to which the cultured periodontal ligament cell sheet in this invention is applied is not limited. Examples of the method of application of the cultured periodontal ligament cell sheet include a method in which the whole surface of the fixture section of the implant in this invention is covered, and a method in which a part of the surface is covered.

The temperature responsive polymer to be used for coating the base material in the cell culture support has an upper critical solution temperature or a lower critical solution temperature of 0° C. to 80° C., more preferably 20° C. to 50° C., in an aqueous solution. In cases where the upper critical solution temperature or the lower critical solution temperature exceeds 80° C., cell death may occur, which is not preferred. In cases where the upper critical solution temperature or the lower critical solution temperature is lower than 0° C., the cell growth rate is extremely low in general, or cell death may occur, which is also not preferred.

The temperature responsive polymer to be used in this invention may be either a homopolymer or a copolymer. Examples of such a polymer include the polymer described in JP 2-211865 A. More specifically, for example, the polymer can be obtained by homopolymerization or copolymerization of the following monomers. Examples of the monomers that may be used include (meth)acrylamide compounds, N-(or N,N-di)alkyl-substituted (meth)acrylamide derivatives, and vinyl ether derivatives. In cases of a copolymer, two or more of these may be arbitrarily selected. Copolymers with monomers other than the monomers described above, grafts and copolymers of polymers, and mixtures of polymers and copolymers may also be used. Poly(N-isopropylacrylamide) is especially preferred. Cross-linking may also be carried out as long as intrinsic properties of the polymer are not deteriorated.

Examples of the base material to which the coating is applied include compounds usually used for cell culture, such as glasses, modified glasses, polystyrenes, and polymethyl methacrylates; and any substances that can generally have shapes, such as macromolecular compounds other than those described above, and ceramics.

The method for coating the support with the temperature responsive polymer is not limited. Examples of the method include the method described in JP 2-211865 A. That is, the coating can be carried out by subjecting the base material, and the monomers and/or polymer(s), to any of electron beam irradiation (EB), γ-ray irradiation, ultraviolet irradiation, plasma treatment, corona treatment, and organic polymerization reaction, or by physical adsorption such as application or kneading.

The coating amount of the temperature responsive polymer is preferably within the range of 0.5 to 5.0 $\mu g/cm^2$, more preferably within the range of 1.0 to 4.0 $\mu g/cm^2$, still more preferably within the range of 1.2 to 3.5 $\mu g/cm^2$. In cases where the coating amount is less than 0.5 $\mu g/cm^2$, detachment of the cells on the polymer is difficult even by stimulation, so that the work efficiency is remarkably low, which is not preferred. On the other hand, in cases where the coating amount is not less than 5.0 $\mu g/cm^2$, attachment of cells on the area is difficult, so that sufficient attachment of the cells is difficult. The shape of the support in this invention is not limited. Examples of the support include dishes, multiplates, flasks, and cell inserts.

The cell culture in this invention may be carried out on a cell culture support produced as described above. In cases where the polymer with which the surface of the base material is coated has an upper critical solution temperature, the temperature of the medium is not limited as long as it is not more than this temperature. In cases where the polymer has a lower critical solution temperature, the temperature of the medium is not limited as long as it is not less than this temperature. However, culture at a temperature within a low-temperature range in which the cultured cells do not grow, or within a high-temperature range in which the cultured cells die, is inappropriate.

In the method of this invention, for collection of the cultured periodontal ligament cell sheet by detachment from the support material, the cultured periodontal ligament cell sheet may be brought into contact with a carrier, and the temperature of the support material to which the cells are attached may be changed to not less than the upper critical solution temperature or not more than the lower critical solution temperature of the coating polymer of the support base material. By this, the periodontal ligament cell sheet can be detached as it is together with the carrier. The detachment of the sheet may be carried out in the culture medium in which the cells were cultured, or may be carried out in another isotonic solution. The method may be selected depending on the purpose.

In this invention, the detachment of the cell sheet from the carrier may also be carried out after attaching the cell sheet to the fixture section of the implant. The method of the detachment is not limited, and may be a method in which the carrier is wet to weaken adhesion of the cell sheet to the carrier, or a method by cutting using a jig such as a scalpel, scissors, laser beam, plasma wave, or the like. For example, in cases where a cell sheet in close contact with a carrier partially cut as described above is used, the cell sheet may be cut along the border line of the affected area using laser beam or the like. This is advantageous since attachment of the cell sheet to an extra area can be avoided.

The method of fixation of the cultured periodontal ligament cell sheet described in this invention to the implant is not limited. The cell sheet and the implant may be bound to each other by using an adhesive that can be used in vivo, or by suture. Alternatively, since the cultured periodontal ligament cell sheet described in this invention can be quickly engrafted on the implant, the sheet may be simply attached to the implant without using such means. For example, the implant may be placed near the center of the detached cells. By pinching the cells using a forceps or the like and covering the implant with the cells, the implant can be wrapped with the cell sheet.

The layering method for the layered sheet in this invention is not limited. For example, the entire periphery of the implant may be directly wrapped with a cell sheet, and the wrapped implant may be placed on the next cell sheet, followed by further wrapping the wrapped implant with the cell sheet. By repeating this process, the layering can be achieved. By this, a layered sheet composed of about three layers can be prepared.

Alternatively, in cases where the carrier described above is used, the layering may be carried out by the following methods.

(1) A method in which a cell sheet in close contact with a carrier is lifted up, and the sheet is then placed on the next cell sheet such that the cell sheets closely contact each other, followed by recovering the resultant by wrapping the carrier, which is the top layer, with sheet edges, and repeating this process to achieve layering of cell sheets.

(2) A method in which a cell sheet in close contact with a carrier is attached to a cell culture support, and a medium is then added thereto to detach the carrier from the cell sheet, followed by further attaching another cell sheet in close contact with a carrier thereto, and repeating this process to achieve layering of cell sheets.

(3) A method in which a cell sheet in close contact with a carrier is inverted, and the carrier side is fixed on a cell culture support, followed by attaching another cell sheet to the cell-sheet side, detaching the carrier from the cell sheet by adding a medium thereto, further attaching another cell sheet thereto, and repeating this operation to achieve layering of cell sheets.

(4) A method in which cell sheets in close contact with carriers are brought into close contact with each other on the cell-sheet sides.

(5) A method in which a cell sheet in close contact with a carrier is attached to the affected area of the body to adhere the cell sheet to the body tissue, and the carrier is then detached, followed by placing another cell sheet on the cell sheet.

For the purpose of detaching/recovering the cultured periodontal ligament cell sheet in this invention with a high yield, a method in which the cell culture support is lightly tapped or shaken, a method in which the medium is stirred using a pipette, and the like may be used individually or in combination. The cultured cells may be detached/recovered after washing with an isotonic solution or the like, if necessary.

The use of the complex of the implant and cultured periodontal ligament cell sheet described in this invention is not limited. Examples of the use include replacing a tooth lost due to a periodontal disease such as moderate periodontitis or severe periodontitis; severe dental caries; or injury. The lost tooth can be replaced by implanting an implant in which a cultured periodontal ligament cell sheet is in close contact with the fixture section, to jaw bone in the portion where the tooth was lost.

EXAMPLES

This invention is described below in more detail by way of Examples. However, this invention is not limited to the Examples.

Example 1

<Study on Surface Morphology of Titanium>
Object: A histological study was carried out to investigate changes in human periodontal ligament cells caused by using titanium, which has high biocompatibility, having a rough surface morphology as an implant material.
Materials and Methods: As the titanium, a foil-shaped pure titanium (circular shape with 10 μm thickness and 3 mm diameter; manufactured by Test Materials), which can be easily prepared into thin sections, was used. Irregularities were given to the surface of the titanium foil by the following surface treatment methods.

Blasting: Blasting was carried out for both surfaces of the titanium foil using zirconia powder with a particle size distribution of 75 to 106 μm≥95% (TZ-SX-16; Tosoh Corporation).

Acid treatment: The titanium foil was immersed at room temperature for 4 hours in a solution prepared by mixing hydrogen peroxide solution (Kanto Chemical Co., Inc.; 18084-01; Cica first grade, >34.5%) and sulfuric acid (Wako Pure Chemical Industries, Ltd.; 192-04696; special grade, >95%) together at 1:1 (Tavares M G et al., Clin Oral Impl Res, 2007, 18, 452-458).

The titanium foil was then washed with ultrapure water a plurality of times.

FIG. 1 shows results of observation of changes in surfaces of titanium foils subjected to the treatments, which observation was carried out using a scanning electron microscope.

Ra of the untreated titanium foil, which was not subjected to surface treatment (A), was 0.051 μm. In contrast, Ra of the titanium foil subjected to the blasting (B) was 0.506 μm, and Ra of the titanium foil subjected to the acid treatment (C) was 0.703 μm.

The titanium foils subjected to these treatments were autoclaved, and used for experiments.

Each titanium foil treated as described above was wrapped with a human cultured periodontal ligament cell sheet, and implanted to an immune-deficient mouse (BALB/cAJcl-nu/nu; male; 7 to 8 weeks old), followed by carrying out histological observation six weeks later.

The method for preparing the human cultured periodontal ligament cell sheet was as follows.

Frozen human periodontal ligament cells (collection and culture of the human periodontal ligament cells were carried out with approval of the ethical committee of Tokyo Women's Medical University) were thawed, and cultured in a normal medium (αMEM+10% FBS, 1% penicillin/streptomycin). After two times of subculture, the cells were plated at $4 \times 10^4$ cells/dish in a cell culture dish in which the surface of the base material is coated with poly(N-isopropylacrylamide) (UpCell (registered trademark) 3.5-cm dish, CellSeed, CS3017). On Day 2 after the plating, the medium was changed to a calcification-inducing medium (αMEM+50 μg/mL ascorbic acid, 10 mM β-glycerophosphate, 10 nM dexamethasone), and medium replacement was carried out at 3- to 4-day intervals. By two weeks of the culture, a periodontal ligament cell sheet was obtained.

The method for bringing the cell sheet into close contact with the titanium foil was as follows.

The culture supernatant was discarded, and 200 μL of a normal medium was added. In this state, the entire border between the cell sheet and the culture dish was traced with a forceps, and the cell sheet was then left to stand at room temperature for 1 to 5 minutes, followed by confirming detachment of the cell sheet from its edge. After the detachment, contraction of the cell sheet was allowed to proceed slightly, and the titanium foil was then placed on the cell sheet. The edge of the cell sheet was lifted up using a forceps, and placed on the titanium foil such that the titanium foil was wrapped therewith. The sheet was then left to stand as it is in the culture medium for 2 to 3 hours to achieve the close contact.

The method for implanting the titanium foil to the mouse was as follows.

An incision with a width of about 1 cm was made on the dorsal skin of the mouse to prepare a subcutaneous pocket, and the titanium foil to which the cell sheet is in close contact was inserted therein, followed by suture. Five to six weeks after the implantation, the mouse was sacrificed by cervical dislocation, and the implanted area was collected together with the surrounding skin.

A tissue sample was prepared as follows.

The collected specimen was immersed in 4% paraformaldehyde (PFA) for 2 to 3 hours, and then washed with water. The specimen was then immersed in an embedding agent for preparation of frozen sections (SCEM, Leica Microsystems, 8091140), and transferred to a stainless steel basket for cryoembedding. After further addition of SCEM, cryoembedding was performed with dry ice/hexane. Using a tungsten blade (TC65, Leica Microsystems), the specimen was sliced to a thickness of 10 µm.

In terms of the staining, hematoxylin-eosin (HE) staining was carried out for observation of the basic tissue structure; Azan staining was carried out for observation of collagen fibers, which are the major component of the periodontal ligament tissue; and Alizarin red staining was carried out for observation of cementum-containing hard tissues.

Figure 2:
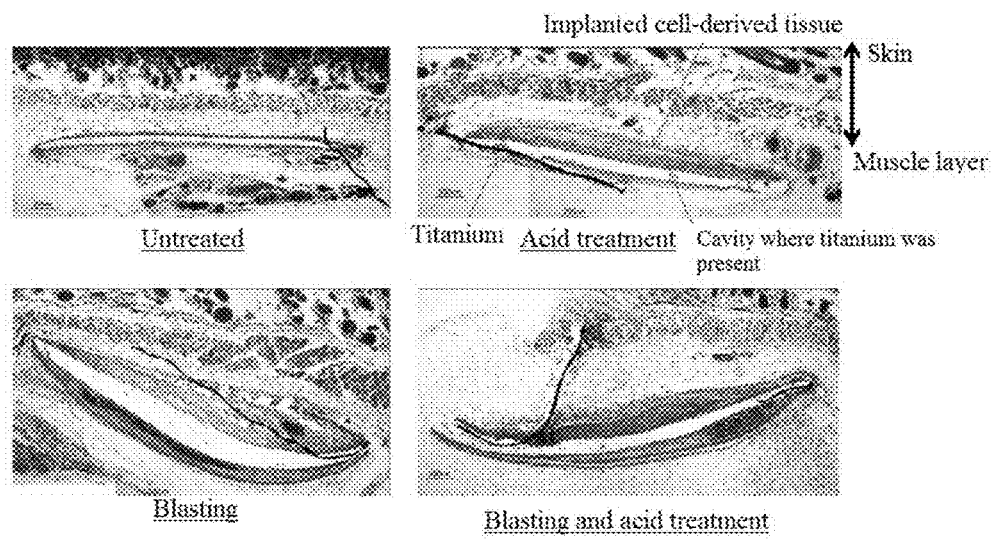
FIG. 2 shows photographs of mouse dorsal subcutaneous tissues, which were taken after Azan staining 6 weeks after implantation of titanium foils. Upper left panel: untreated; upper right panel: after acid treatment; lower left panel: after blasting; lower right panel: after blasting and acid treatment.

The results of the Azan staining are shown in FIG. 2.

Collagen fibers, which are stained in blue, were clearly observed in all groups. Since the collagen fibers are a fibrous component contained in the periodontal ligament tissue, it can be said, based on FIG. 2, that, by the close contact of the cultured periodontal ligament cell sheet to the periphery of the titanium foil, the titanium favorably adhered to the surrounding tissue via a periodontal ligament-like tissue.

The periodontal ligament-like tissue layer derived from the implanted cells, found on the periphery of the titanium foil, was significantly thicker in the group in which the blasting was carried out.

Figure 3:
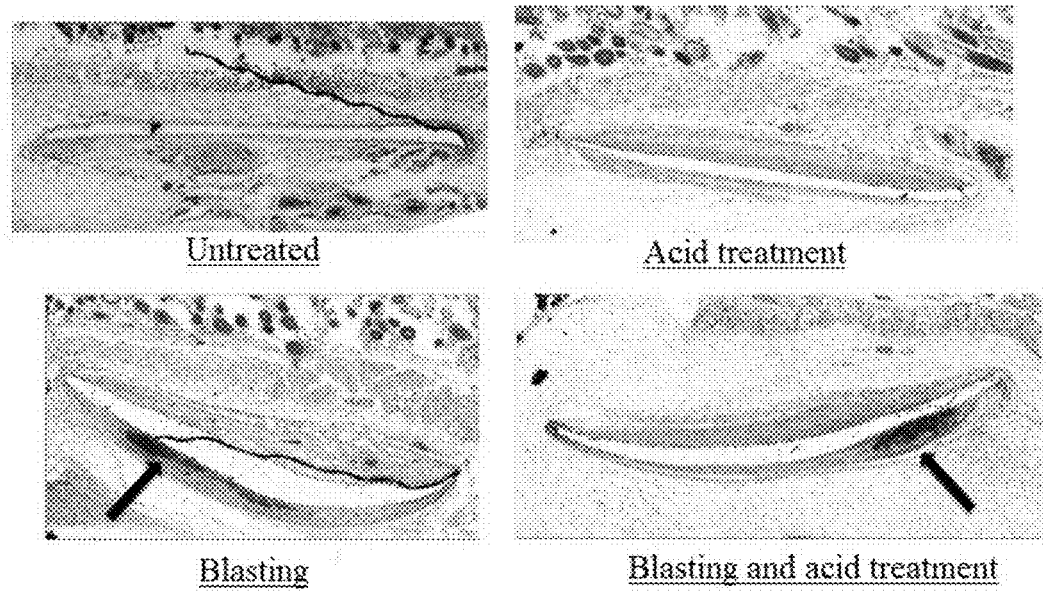
FIG. 3 shows photographs of mouse dorsal subcutaneous tissues, which were taken after Alizarin red staining 6 weeks after implantation of titanium foils. Upper left panel: untreated; upper right panel, after acid treatment; lower left, after blasting; lower right, after blasting and acid treatment.

The results of the Alizarin red staining are shown in FIG. 3.

In FIG. 3, the red portions indicated by the black arrowheads are calcified areas. In each of the groups in which the blasting was carried out, a calcified layer which is a cementum-like tissue was found.

Figure 4:
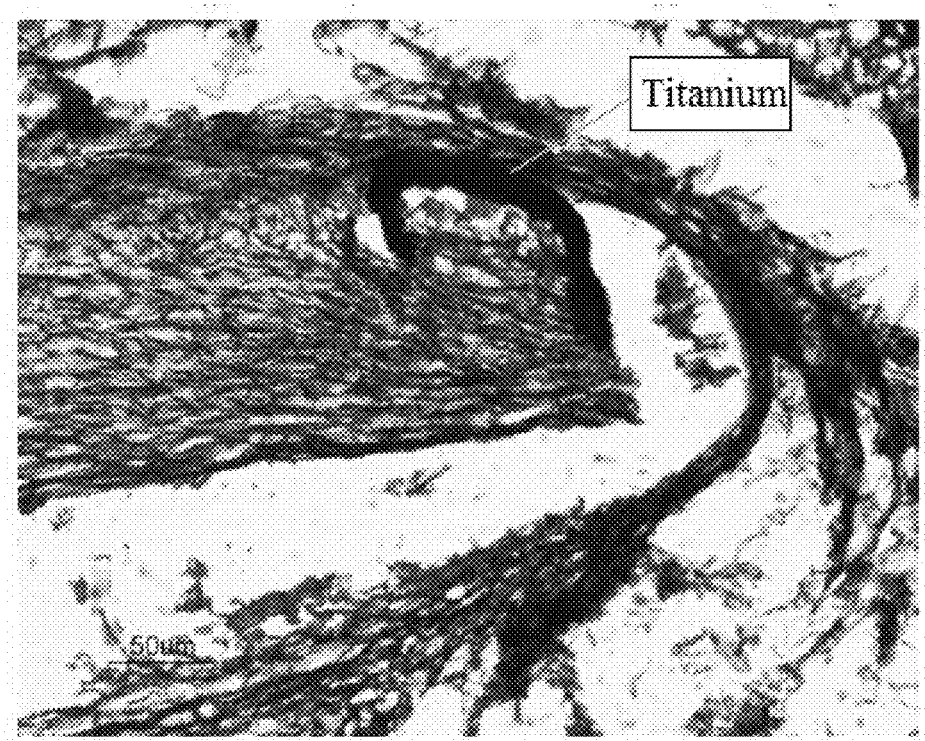
FIG. 4 shows a photograph of a mouse dorsal subcutaneous tissue, which was taken after Azan staining 6 weeks after implantation of a titanium foil that was subjected to blasting and acid treatment, and folded into a U-shape.

A run of collagen fibers similar to the run of a physiologically normal periodontal ligament tissue is shown in FIG. 4.

FIG. 4 shows a photograph, taken after Azan staining, of a tissue obtained from a mouse implanted with a titanium foil having a surface subjected to blasting and acid treatment, which titanium foil was formed to have a U-shape with a width of 50 µm by folding of its both ends. It was observed, from this photograph, that periodontal ligament-like fibers are running such that they form connections in the U-shaped titanium foil.

Example 2

<Study on Calcium Phosphate (CaP) Coating>
Object: For achievement of better cell adhesion, blasting and acid treatment as well as coating with calcium phosphate were carried out, and changes in the cell adhesion were observed.
Methods: The blasting and the acid treatment described in Example 1 as well as coating with calcium phosphate were carried out.

The method for the coating with calcium phosphate was as follows.

Hanks solution (glucose-free: $Na^+$ $1.42\times10^{-1}$ mol/L, $K^+$ $5.81\times10^{-3}$ mol/L, $Mg^{2+}$ $8.11\times10^{-4}$ mol/L, $Ca^{2+}$ $1.26\times10^{-3}$ mol/L, $Cl^+$ $1.45\times10^{-1}$ mol/L, $HPO_4^{2-}$ $7.78\times10^{-4}$ mol/L, $SO_4^{2-}$ $8.11\times10^{-4}$ mol/L, $CO_3^{2-}$ $4.17\times10^{-3}$ mol/L) was prepared by the following procedure.

After addition of 8.00 g of NaCl (Wako Pure Chemical Industries, Ltd., 101-01665), 0.40 g of KCl (Wako Pure Chemical Industries, Ltd., 163-03545), 0.06 g of $Na_2HPO_4.2H_2O$ (MERCK, 1.06580.0500: product number 106580), 0.06 g of $KH_2PO_4$ (Kanto Chemical Co., Inc., 32379-00), 0.20 g of $MgSO_4.7H_2O$ (Kanto Chemical Co., Inc., 25034-00), and 0.35 g of $NaHCO_3$ (Kanto Chemical Co., Inc., 37116-00) to a 1-L measuring flask containing 500 ml of pure water, the resulting mixture was stirred to allow dissolution of the reagents. Thereafter, 0.14 g of $CaCl_2$ (Kanto Chemical Co., Inc., 07057-00) was added to the solution, and pure water was added to the resulting mixture to attain a final volume of 1 L, followed by stirring the mixture to allow dissolution of the reagent. The pH after the dissolution was measured. As a result, the pH was found to be 7.4.

In the Hanks solution prepared, a titanium foil was placed and then kept immersed at 310 Kelvin (K) for 378 hours. The foil was then washed with ethanol, and subjected to sterilization by autoclaving before use.

Figure 5:
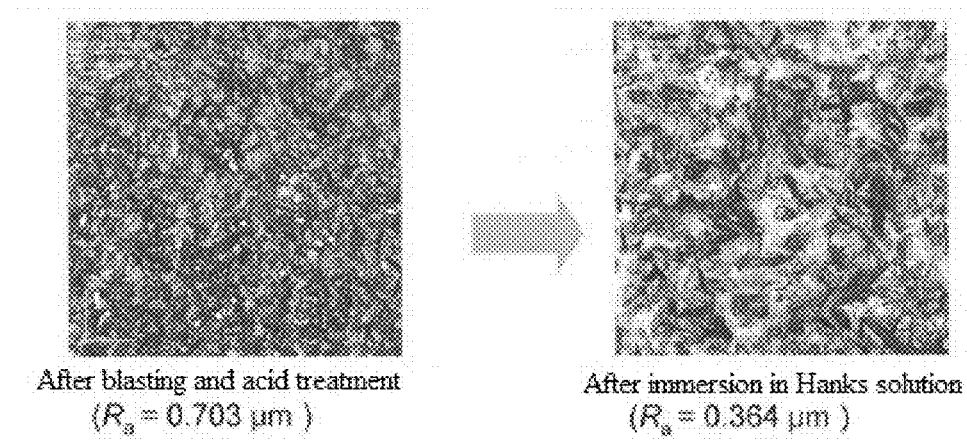
FIG. 5 shows a scanning electron micrograph showing a change in the surface of a titanium foil coated with calcium phosphate. Left panel: after blasting and acid treatment; right panel: blasting, acid treatment, and coating with calcium phosphate (after immersion in Hanks solution).

FIG. 5 shows the result of observation of the change in surface of the titanium foil after the immersion in Hanks solution, which observation was carried out using a scanning electron microscope.

Ra of the titanium foil after the blasting and the acid treatment was 0.703 µm. In contrast, Ra of the titanium foil after the immersion in Hanks solution was 0.364.

The methods for the implantation and the like were the same as those in Example 1. The obtained tissue sample was observed after staining with Azan.

Figure 6:
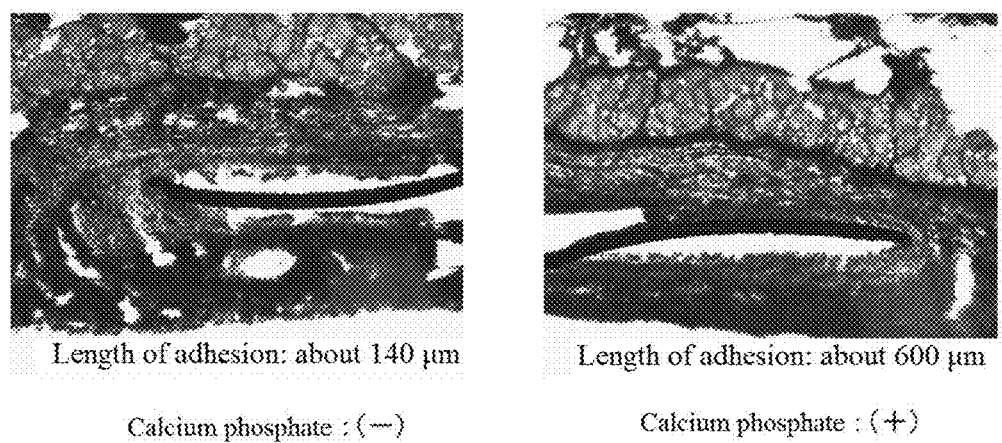
FIG. 6 shows photographs of a mouse dorsal subcutaneous tissue, which was taken after Azan staining 6 weeks after implantation of a titanium foil coated with calcium phosphate. Left panel: no coating with calcium phosphate; right panel: coating with calcium phosphate.

The result of the Azan staining is shown in FIG. 6.

Unlike the group without the calcium phosphate coating (left panel in FIG. 6), the group in which the coating was carried out showed significant adhesion of cells to the titanium, and formation of abundant collagen fibers in its vicinity (right panel in FIG. 6).

Thus, it was shown that the coating with calcium phosphate improves adhesion of the cells. It was also shown that blasting and/or acid treatment is/are appropriate as a pretreatment(s) for the coating.

Example 3

<Implantation into Rat Femur>
Object: Rod-shaped titanium was used instead of foil-shaped titanium, and implantation into bone was carried out instead of subcutaneous implantation. By this, adhesion of the cells to the titanium can be investigated under conditions that are more similar to those for implantation into jaw bone. Titanium in close contact with a cell sheet was implanted into rat femur.
Methods: Rod-shaped titanium (1 mm diameter, 3 mm length) having no screw thread was subjected to blasting and acid treatment. A comparison was made between cases where calcium phosphate coating was carried out and cases where calcium phosphate coating was not carried out.

Figure 7:
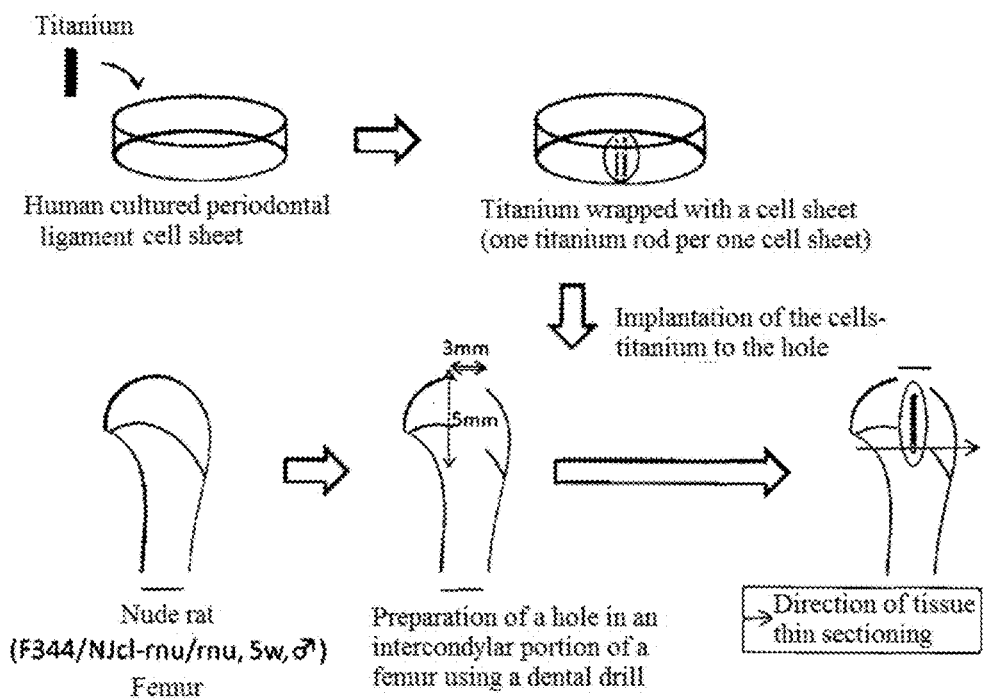
FIG. 7 shows a procedure for implantation of a titanium rod into rat femur.

The cultured periodontal ligament cell sheet used was the same as those used in the experiments described above. FIG. 7 shows a summary of the experiment method.

Immune-deficient mice (F344/NJcl-rnu/rnu, 5w, male) were used as animals for implantation. A defect with a size of 3 mm diameter and 5 mm length was prepared from the femoral head under anesthesia using a dental engine. The titanium rod in close contact with the cell sheet was implanted into the defect. Six weeks after the implantation, the tissue was recovered together with the bone, and fixed with 4% PFA, followed by preparation of frozen sections in the same manner as in Example 1. After HE staining, morphological observation was carried out. Part of the samples in the calcium phosphate coating group were fixed with 2.5% glutaraldehyde, and embedded in Epon resin after removal of the titanium. Observation was carried out after staining with toluidine blue. Further observation was carried out using a transmission electron microscope.

In addition, six weeks after the implantation, the tissue was recovered together with the bone, and fixed with 70% ethanol, followed by being embedded in MMA resin. After preparation of a polished sample, Villanueva Goldner staining was carried out, and the stained sample was observed under a light microscope.

Figure 8:
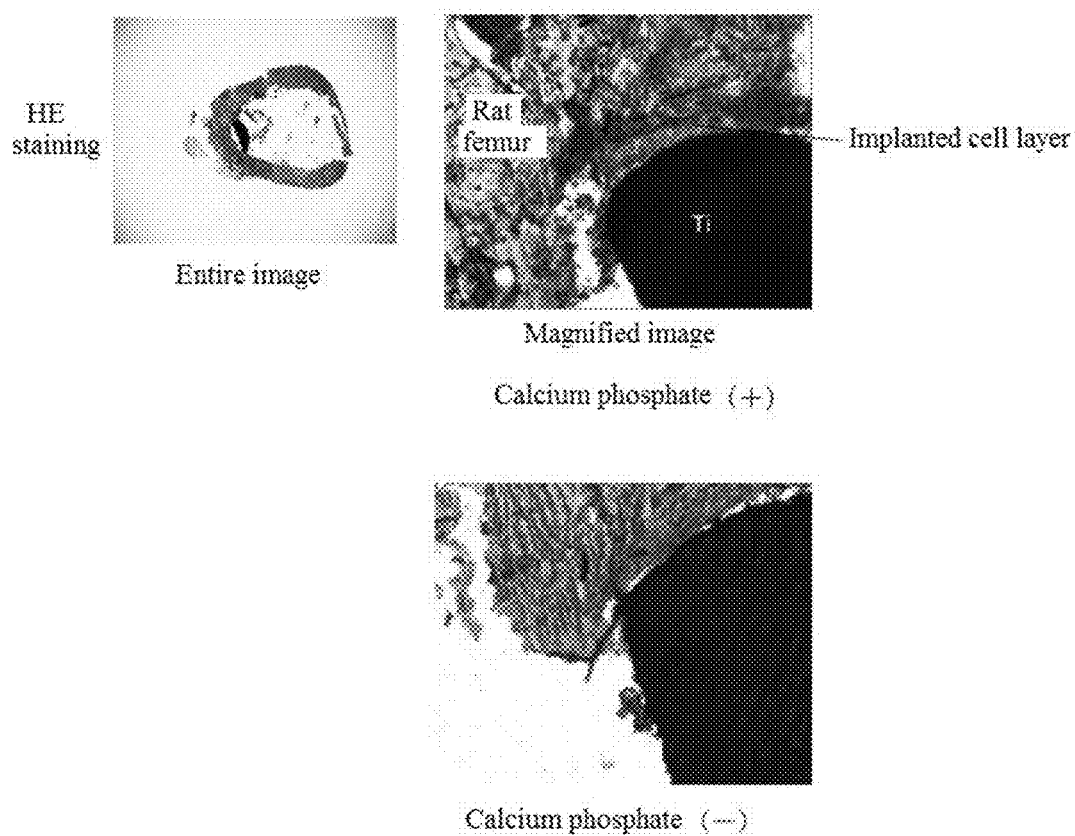
FIG. 8 shows photographs of rat femur, which were taken after hematoxylin-eosin staining 6 weeks after implantation of a titanium rod. Left panel: a cross-section of the portion containing the titanium rod in the femur. Upper right panel: coating with calcium phosphate; lower right panel: no coating with calcium phosphate.

FIG. 8 shows the result of the HE staining.

In the calcium phosphate coating group, an implanted cell layer was found at positions where the distance between the femur and the titanium was about 20 µm. At positions where the bone and the titanium are more distant from each other, the implanted cell layer could be hardly observed. On the other hand, in the group without calcium phosphate coating, no cell layer was found between the bone and the titanium even at positions where they are close to each other, and the bone and the titanium seemed to be adhering to each other.

Figure 9:
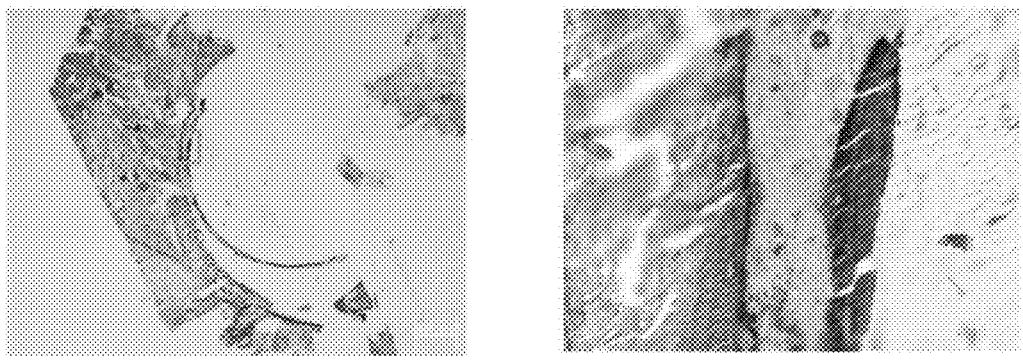
FIG. 9 shows photographs of rat femur, which were taken after toluidine blue staining 6 weeks after implantation of a titanium rod. The right photograph is an enlarged photograph of the area surrounded by the orange-colored frame in the left photograph.

FIG. 9 shows the result of the toluidine blue staining in the group in which the calcium phosphate coating was carried out.

As a result of observation after removal of the titanium, formation of a thin calcified layer was found along the shape of the titanium. The area of the newly generated calcified layer was found to be similar to cementum. As a result of observation of an area where the distance between the bone and the titanium was about 20 µm, a cell layer was found between the bone and the newly generated hard tissue, as was observed by the HE staining.

Figure 10:
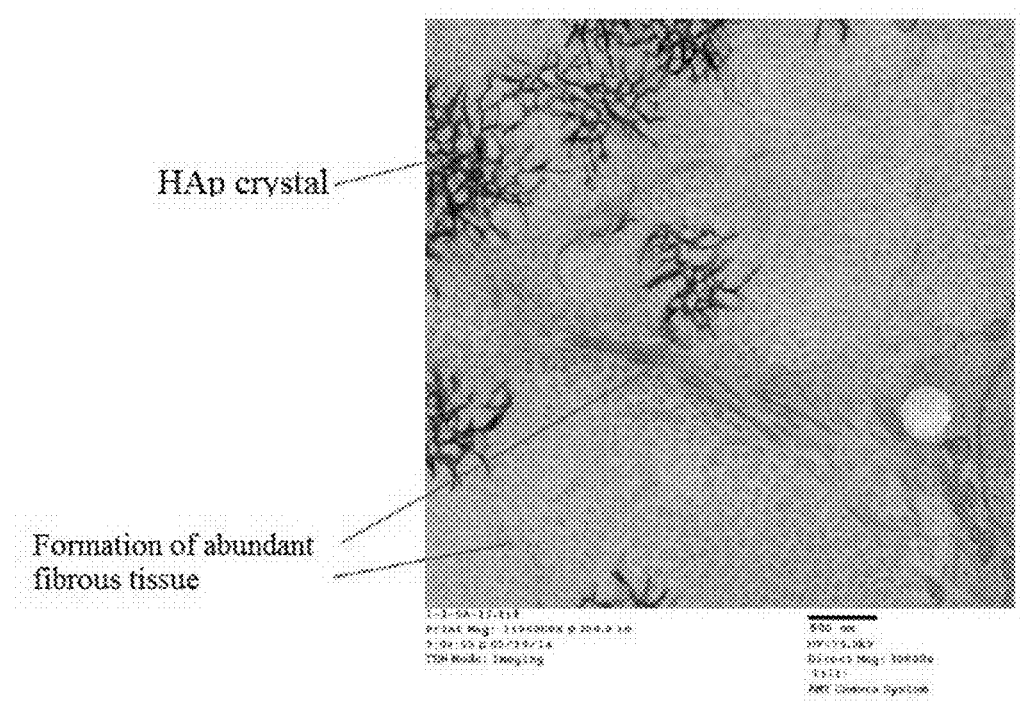
FIG. 10 shows a transmission electron micrograph of rat femur, which was taken 6 weeks after implantation of a titanium rod.

Further, when an area of the cell layer in the group subjected to the calcium phosphate coating was observed under magnification using an electron microscope (FIG. 10), formation of an abundant fibrous tissue was found. This is considered to be due to formation of abundant collagen fibers, which are the main component of the periodontal ligament tissue. Further, hydroxyapatite crystals, which indicate calcification, were found in many areas.

Figure 11:
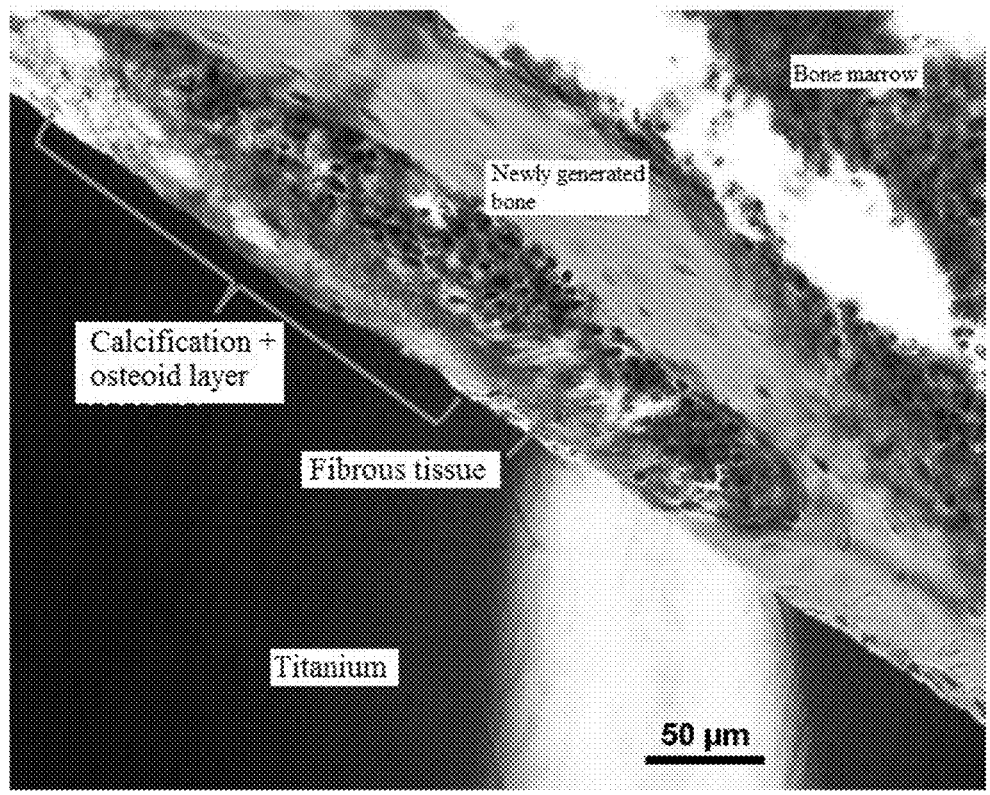
FIG. 11 shows an image (photograph) of rat femur, which was taken after Villanueva Goldner staining 6 weeks after implantation of a titanium rod.

FIG. 11 shows the result of the Villanueva Goldner staining. In the calcium phosphate coating group, a space was formed between the titanium and the newly generated bone, and a calcified layer or an osteoid layer was formed on the titanium surface in the space. Fibrous connective tissues were found to be running such that they connect the calcified layer or the osteoid layer to the newly generated bone. This run was similar to that found in the vicinity of a natural tooth, wherein a periodontal ligament tissue runs such that cementum on the root surface is connected to alveolar bone.

Example 4

Figure 12:
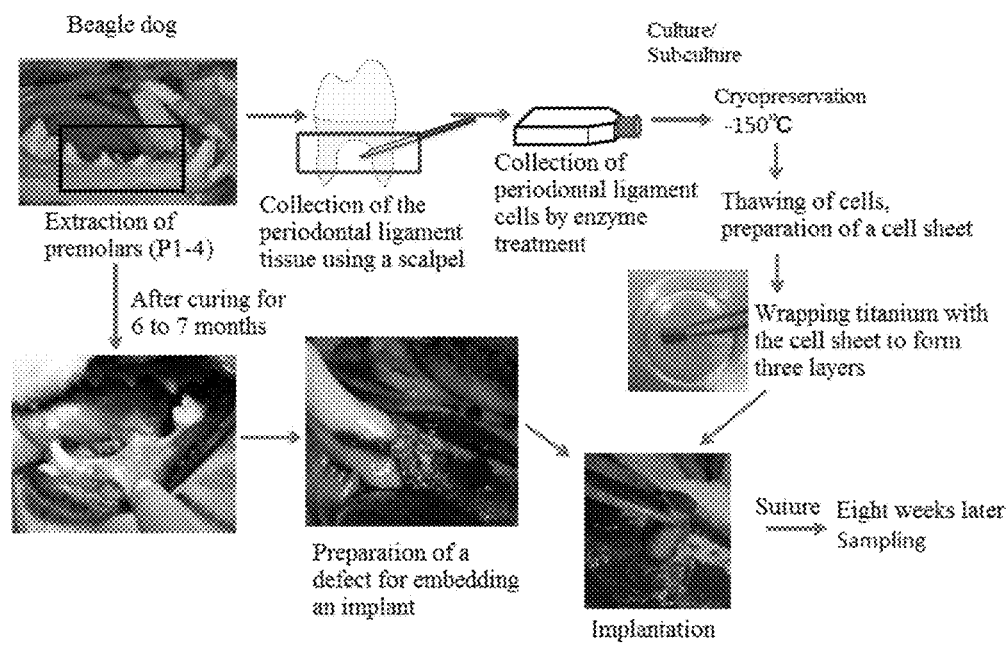
FIG. 12 shows a schematic diagram showing an experiment by implantation to a beagle dog.

<Implantation to Dog Jaw Bone with Tooth Loss>
Object: A dog was used as a large animal which is closer to human. A cultured periodontal ligament cell sheet was brought into close contact with the fixture section of a rod-shaped implant, and the resultant was implanted into dog jaw bone in which a tooth was lost. Effectiveness of the implantation was observed.
Methods: An implant having a rod-shaped titanium fixture section with no screw thread (having a shallow conical shape with a diameter of 3.5 mm in the upper end and 3 mm in the lower end; 8 mm length) was subjected to blasting and acid treatment of the fixture section. The fixture section was then subjected to calcium phosphate coating treatment, and a cultured periodontal ligament cell sheet was brought into close contact with the fixture section. FIG. 12 shows a summary of the experiment method.

Figure 13:
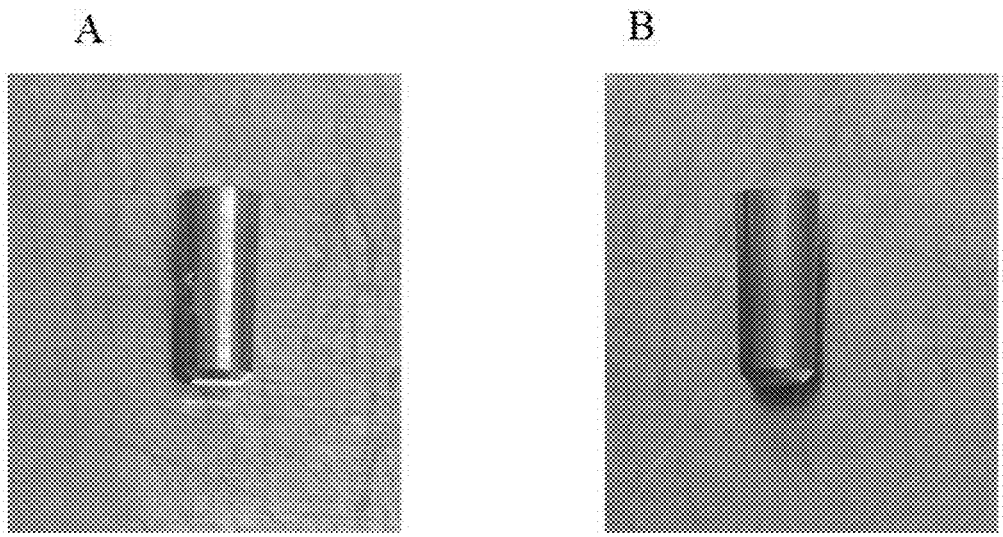
FIG. 13 shows implants implanted to a beagle dog (photographs). Panel A shows a titanium implant prepared, and Panel B shows a titanium implant prepared by subjecting the implant shown in Panel A to blasting, acid treatment, and coating with calcium phosphate.

An implant having a rod-shaped titanium fixture section with no screw thread (having a shallow conical shape with a diameter of 3.5 mm in the upper end and 3 mm in the lower end; 8 mm length) as shown in FIG. 13 was prepared. This implant was prepared assuming a dental implant which can be practically used at clinical situations from the viewpoints of the shape, size, material, and the like. Only the fixture section of the implant was subjected to blasting and acid treatment, and further to calcium phosphate coating treatment. The blasting and the acid treatment were carried out by the same methods as described in Example 1. The calcium phosphate coating treatment was carried out by the same method as described in Example 2.

A dog cultured periodontal ligament cell sheet was obtained by the following method. A premolar was extracted from a dog (beagle, male, 2 years old) under anesthesia, and a periodontal ligament tissue was collected from the root of the extracted tooth obtained. The tissue was subjected to collagenase/dispase treatment with shaking (treatment conditions: 37° C., 45 minutes) to obtain dog periodontal ligament cells, and the cells were cryopreserved until use (collection and culture of the cells were carried out with approval of the ethical committee of Tokyo Women's Medical University). Two weeks before the implantation, the frozen dog periodontal ligament cells were thawed, and cultured in a normal medium (αMEM+10% FBS, 1% penicillin/streptomycin). After two times of subculture, the cells were plated at $4 \times 10^4$ cells/dish in a cell culture dish in which the surface of the base material is coated with poly(N-isopropylacrylamide) (UpCell (registered trademark) 3.5-cm dish, CellSeed; amount of poly(N-isopropylacrylamide) coating, 2.0 µg/cm$^2$). On Day 2 after the plating, the medium was changed to a calcification-inducing medium (αMEM+ 50 µg/mL ascorbic acid, 10 mM β-glycerophosphate, 10 nM dexamethasone), and medium replacement was carried out at 3- to 4-day intervals. By six days of the culture, a periodontal ligament cell sheet was obtained.

Figure 14:
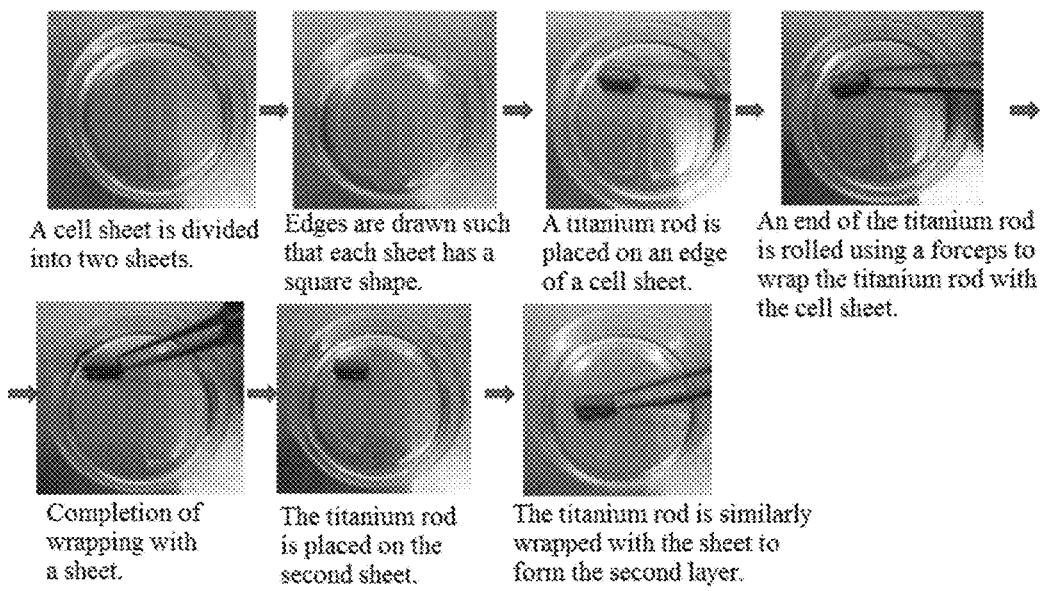
FIG. 14 shows a diagram showing a procedure for wrapping an implant with a cultured periodontal ligament cell sheet. This procedure was repeated to finally form three layers before implantation.

The dog periodontal ligament cell sheet obtained by the above culture was brought into close contact with the periphery of the fixture section subjected to the above treatments, by wrapping the fixture section with the cell sheet to form three layers of the cell sheet (FIG. 14), to obtain the complex of implant and cultured periodontal ligament cell sheet. Six months after the extraction of the tooth, when the extraction wound was almost repaired, implantation into dog jaw bone was carried out according to the following method.

Figure 15:
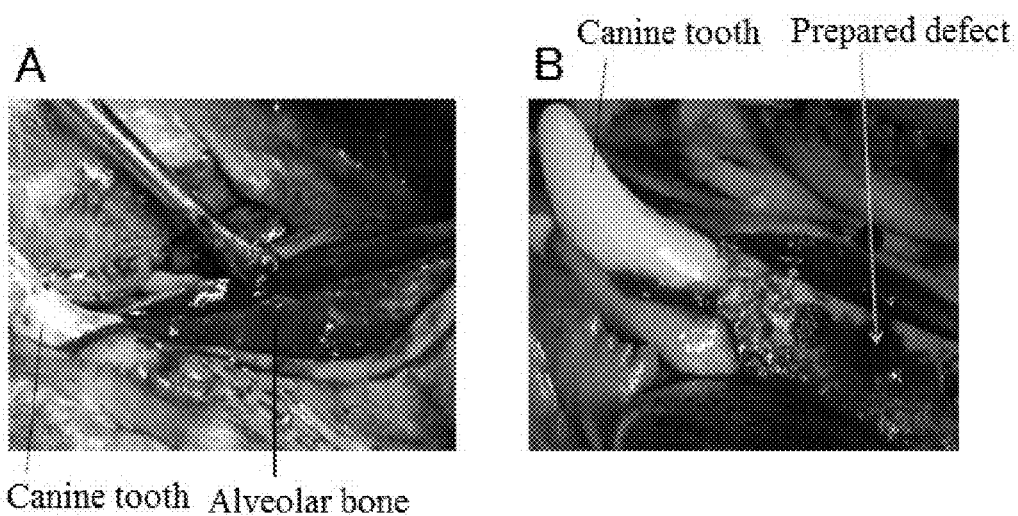
FIG. 15 shows photographs showing preparation of a defect for inserting an implant in a beagle dog. Panel A shows a photograph taken 6 months after tooth extraction, before preparation of the defect. Panel B shows preparation of the defect for inserting an implant.
Figure 16:
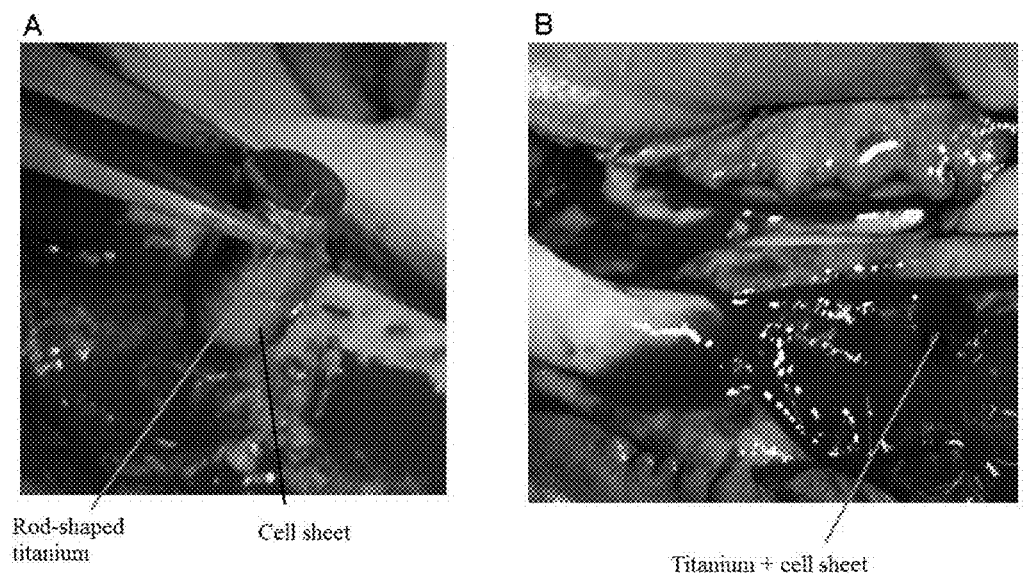
FIG. 16 shows photographs showing completion of inserting of an implant in a beagle dog. Panel A shows inserting of titanium to which a cell sheet is attached, and Panel B shows completion of the inserting of the titanium to which the cell sheet is attached.
Figure 17:
FIG. 17 shows a photograph showing suture of a portion where an implant was embedded in a beagle dog.

According to a conventional method, a defect (about 4.5 mm in diameter, and about 8 to 10 mm in length) for inserting an implant, having a diameter slightly larger than that of the implant body, was prepared under anesthesia in the alveolar bone after curing of the tooth extraction (FIG. 15). The complex of the implant and cultured periodontal ligament cell sheet in which the implant was wrapped with the periodontal ligament cell sheet was subjected to additional culture for about one hour, and then gently implanted into the thus prepared defect (FIG. 16), followed by suturing the surrounding gingiva to finish the experiment (FIG. 17).

Figure 18:
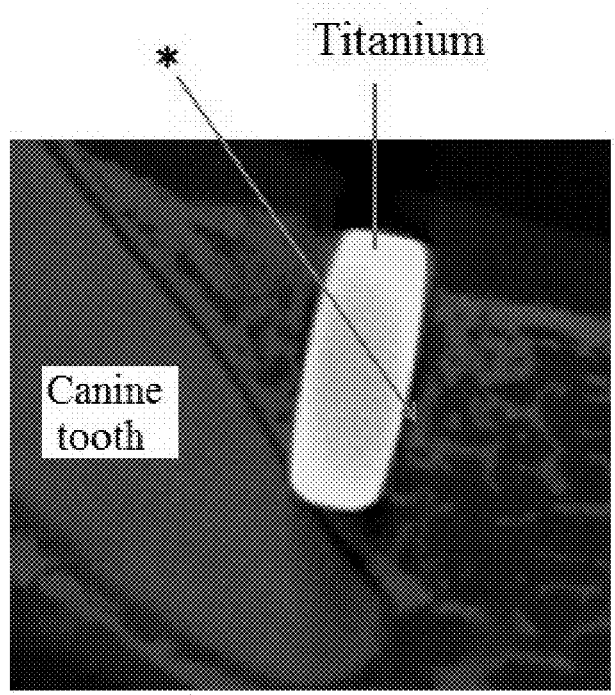
FIG. 18 shows a CT image taken 8 weeks after inserting of an implant in a beagle dog. The symbol * indicates a portion where no adhesion between bone and titanium was found, and a periodontal ligament space-like X-ray transmission image was obtained.

Eight weeks after the implantation, the implant implanted to the jaw bone was favorably stabilized to the jaw bone. On a CT image (FIG. 18), a space was found between the inserted implant and the surrounding alveolar bone. In conventional implant treatment, adhesion of an implant body to jawbone occurs, and no space is found on an X-ray image. Regeneration of a periodontal tissue on the implant was therefore impossible. Thus, the space between the implant and the surrounding alveolar bone suggests the possibility of successful construction of a physiologically normal periodontal tissue on the implant. No abnormality was found in the surrounding gingiva.

From the above results, it was shown that, by bringing a cultured periodontal ligament cell sheet into close contact with an implant, favorable adhesion of the implant to alveolar bone can be achieved via a periodontal ligament-like tissue. It was further shown that, by bringing a cultured periodontal ligament cell sheet into close contact with an implant subjected to blasting, acid treatment, and/or calcium phosphate coating, and implanting the resultant into a bone tissue, a cementum-like tissue can be formed. The implant wrapped with the cultured periodontal ligament cell sheet in this invention was shown to be useful as a novel therapeutic method.

INDUSTRIAL APPLICABILITY

An implant in close contact with a cultured periodontal ligament cell sheet prepared by this invention can be engrafted to the surrounding bone via a cementum-like hard tissue and a periodontal ligament-like tissue formed in its adjacent. Positive reconstruction of a periodontal tissue is possible by the implanted periodontal ligament cells. Further, by layering the cell sheets to be implanted on each other to give a three-dimensional polarity thereto, more efficient reconstruction of the attached organ is possible, so that clinical application of this invention as a therapeutic method for replacing a tooth lost due to moderate periodontitis, severe periodontitis, severe dental caries, injury, or the like can be strongly expected. Even in cases where inflammation occurred, the self-defending capacity and the immune mechanism retained in the periodontal ligament tissue can act to control peri-implantitis. Thus, this invention is very useful in the fields of medicine and biology, including cell engineering and medical engineering.

The invention claimed is:

1. A complex of implant and cultured periodontal ligament cell sheet, wherein said implant contains a fixture section; the surface of said fixture section is roughened, and wherein said roughened surface of said fixture section is coated with calcium phosphate; the cultured periodontal ligament cell sheet is attached to the roughened surface of said fixture section; and, wherein said cultured periodontal ligament cell sheet is a calcification-induced cultured periodontal ligament cell sheet, wherein said cultured periodontal ligament cell sheet is obtained by culturing periodontal ligament cells on a cell culture support formed by coating a surface of a base material with a temperature responsive polymer of which upper or lower critical solution temperature against water is 0 to 80° C., and detaching the cultured cells by changing the temperature of a culture medium to not less than the upper critical solution temperature or to not more than the lower critical solution temperature, and wherein the material of said fixture section is metal.

2. The complex of the implant and cultured periodontal ligament cell sheet according to claim 1, wherein said temperature responsive polymer is poly(N-isopropylacrylamide).

3. The complex of the implant and cultured periodontal ligament cell sheet according to claim 1, wherein said calcification-induced cultured periodontal ligament cell sheet is a periodontal ligament cell sheet cultured in a medium containing dexamethasone, ascorbic acid, and β-glycerophosphate.

4. The complex of the implant and cultured periodontal ligament cell sheet according to claim 1, wherein said cultured periodontal ligament cell sheet is layered.

5. The complex of the implant and cultured periodontal ligament cell sheet according to claim 1, wherein the surface of said fixture section is roughened by blasting and acid treatment, said surface having an arithmetic average roughness (Ra) of 0.1 to 1.0 μm.

6. The complex of the implant and cultured periodontal ligament cell sheet according to claim 1, wherein the material of said fixture section is titanium.

7. The complex of the implant and cultured periodontal ligament cell sheet according to claim 1, wherein said fixture section has a cylindrical shape.

8. A method for treating a lost tooth comprising replacing a lost tooth with the complex of the implant and cultured periodontal ligament cell sheet according to claim 1.

9. The method according to claim 8, wherein said treatment comprises attaching a cultured periodontal ligament cell sheet to a dental implant fixture section to form a complex of the cultured periodontal ligament cell sheet and the dental implant fixture section, and implanting the obtained complex to jaw bone.

* * * * *